(12) United States Patent
Kim et al.

(10) Patent No.: US 6,368,993 B1
(45) Date of Patent: Apr. 9, 2002

(54) METHOD OF FABRICATING A SINTERED CERAMIC COMPOSITE

(75) Inventors: Hyoun Ee Kim, Daewoo Apt. 1-308, Bangbae-Dong, Seocho-Ku; Young Min Kong; In Seop Lee, all of Seoul (KR)

(73) Assignee: Hyoun Ee Kim, Seoul (KR)

( * ) Notice: Subject to any disclaimer, the term of this patent is extended or adjusted under 35 U.S.C. 154(b) by 0 days.

(21) Appl. No.: 09/469,077

(22) Filed: Dec. 21, 1999

(51) Int. Cl.[7] .......................... C04B 35/80; C04B 35/81
(52) U.S. Cl. ............................ 501/95.2; 501/1; 501/87; 501/97.1; 501/95.3; 264/125; 264/641
(58) Field of Search .................... 501/1, 87, 95.2, 501/95.3, 97.1; 623/23.56; 264/641, 125

(56) References Cited

U.S. PATENT DOCUMENTS

| | | | | |
|---|---|---|---|---|
| 4,772,573 A | * | 9/1988 | Toriyama et al. | 501/1 |
| 4,897,370 A | * | 1/1990 | Horiguchi et al. | 501/5 |
| 4,960,733 A | * | 10/1990 | Kasuga et al. | 501/10 |
| 5,032,552 A | * | 7/1991 | Nonami et al. | 501/95 |
| 5,082,808 A | * | 1/1992 | Nonami et al. | 501/1 |
| 5,091,344 A | * | 2/1992 | Enomoto et al. | 501/1 |
| 5,204,319 A | * | 4/1993 | Enomoto et al. | 501/1 |
| 5,232,878 A | * | 8/1993 | Kasuga et al. | 501/10 |

FOREIGN PATENT DOCUMENTS

| | | | |
|---|---|---|---|
| JP | 02124775 | * | 5/1990 |
| WO | WO93/20018 | * | 10/1993 |

* cited by examiner

*Primary Examiner*—Karl Group
(74) *Attorney, Agent, or Firm*—Scully, Scott, Murphy & Presser

(57) ABSTRACT

The present invention relates to a sintered ceramic composite implant material and a fabrication method thereof. A sintered ceramic composite implant material includes an apatite matrix phase, a ceramic secondary phase located in the apatite matrix phase, a barrier layer coating the ceramic secondary phase. The secondary phase compensates for and improves the mechanical properties of the apatite matrix phase and the barrier layer restrains an interfacial reaction between the apatite matrix phase and the secondary phase.

13 Claims, 7 Drawing Sheets

METHOD OF FABRICATING A SINTERED CERAMIC COMPOSITE

BACKGROUND OF THE INVENTION

1. Field of the Invention

The present invention relates to a ceramic composite and a fabrication method thereof, and in particular to a sintered ceramic composite implant material and a fabrication method thereof.

2. Description of the Background Art

Bioceramic implant material is one of the biomaterials that can be replaced for the damaged human tissues. As a substitute material for damaged teeth or bones, apatite has attracted much attention over the past several decades, because of its crystallographical and chemical similarity with various classified tissues of vertebrates. This ceramic is known to be biocompatible, not harmful to tissues, and to form a direct bond with the neighboring bones. Among the apatites that have above-described properties, a hydroxyapatite (hereinafter, referred to as 'HAp') is most widely used material.

However, the poor mechanical properties of the HAp compared to those of natural bone are one of the most serious obstacles for load-bearing part replacement. As a result, it is only used for inner ear bone and bone filler as a non-load-bearing part implant. In order to replace the load-bearing hard tissue such as hip joint that has high strength and fracture toughness, HAp needs to be composite with other material. That is to say, it is needed to improve the mechanical properties of HAp.

There has been an approach for the improvement in mechanical properties of the HAp; metal implants coated with HAp, which are widely used these days. The metal part is for mechanical properties and HAp part is for bioactivity and biocompatibility of the implant. However, large differences in physical and thermal properties between the metals and the HAp cast limitation to this approach.

SUMMARY OF THE INVENTION

Accordingly, it is an object of the present invention to provide a sintered ceramic composite implant material and a fabrication method thereof which are capable of utilizing the bioactivity and biocompatibility of apatite and of compensating for the poor mechanical properties of apatite.

It is another object of the present invention to provide a sintered ceramic composite implant material and a fabrication method thereof using reinforcement which has similar physical and thermal properties to those of apatite and which are capable of compensating for the poor mechanical properties of apatite without problems caused by differences in physical and thermal properties.

To achieve the above object, there is provided a sintered ceramic composite implant material comprising an apatite matrix phase, and secondary phase composed of ceramic material and located in the apatite matrix phase, and barrier layer coating the secondary phase. The secondary phase improves the mechanical properties of a sintered ceramic composite implant material by compensating for the poor mechanical properties of apatite matrix phase. The barrier layer restrains an interfacial reaction between the apatite matrix phase and the secondary phase.

In another aspect, the present invention contemplates a method for fabricating a sintered ceramic composite implant material, comprising the steps of providing reinforcement powder coated with barrier layer, providing mixed powder by mixing the coated reinforcement powder with apatite powder, sintering the mixed powder. The coated reinforcement powder is provided by making reinforcement powder and barrier layer powder charged with different sign to each other in a suspension.

Additional advantages, objects and features of the invention will become more apparent from the description which follows.

BRIEF DESCRIPTION OF THE DRAWINGS

The present invention will become more fully understood from the detailed description given below and the accompanying drawings, which are given by way of illustration only and are not limitative of the present invention, and wherein.

DETAILED DESCRIPTION OF THE PREFERRED EMBODIMENTS

Figure 1:
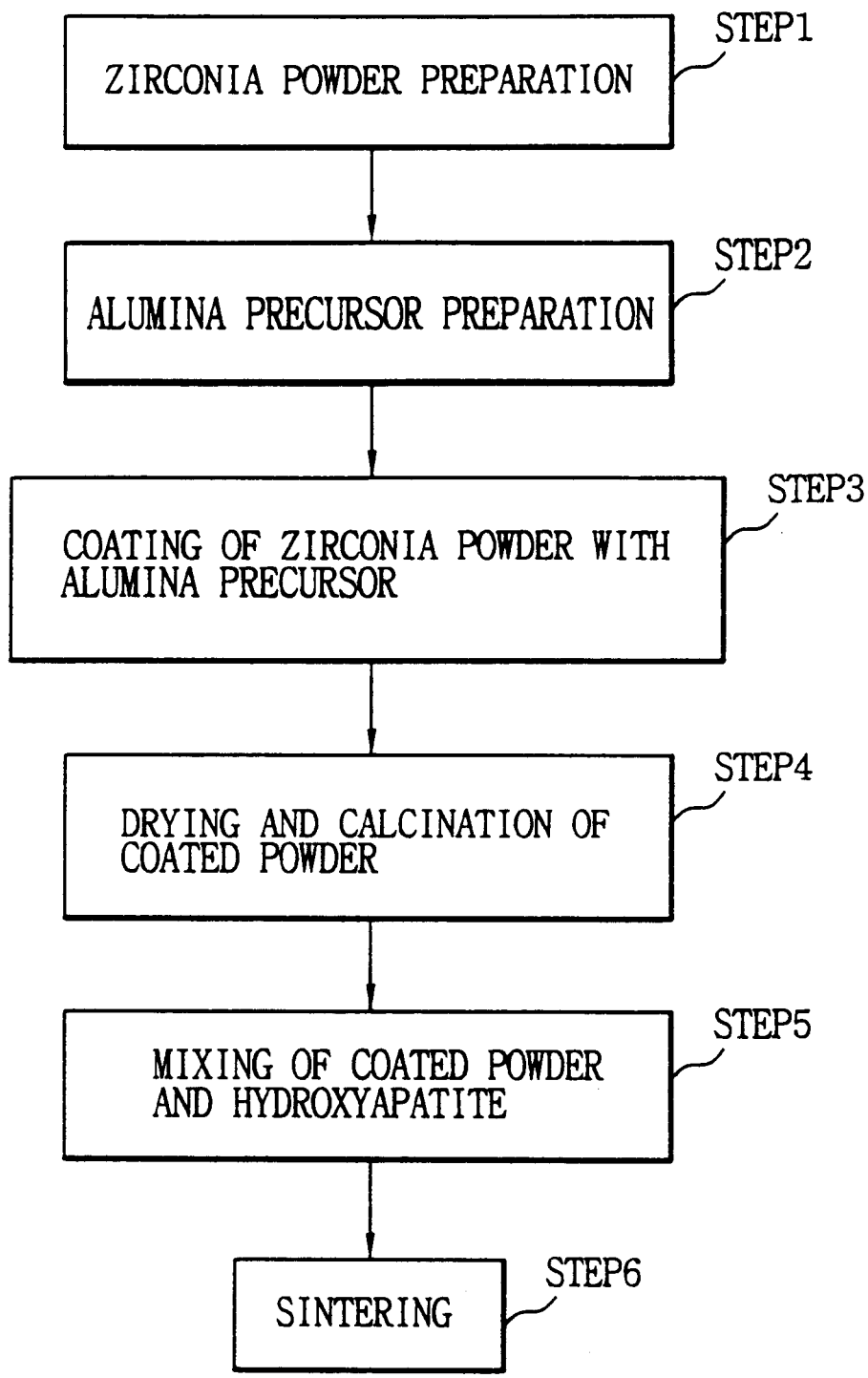
FIG. 1 is a process flow illustrating a method for manufacturing a sintered ceramic composite implant material according to an embodiment of the present invention.

In the present invention, a sintered ceramic composite implant material is provided including apatite as a matrix phase. The apatite is represented by the following formula.

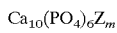

$Ca_{10}(PO_4)_6Z_m$

In the above formula, the 'Z' represents OH, $CO_3$, F, Cl or the mixing of them, and the 'm' represents a number (such as 1,2 etc.) satisfying stoichiometry. Accordingly, HAp, carbonate apatite, fluoroapatite, chloroapatite and their mixtures can be used as a matrix phase according to the present invention. Apatite precursor which can transform into apatite during sintering can also be used as a matrix phase. In particular, HAp is used as a matrix phase according to an embodiment of the present invention.

The HAp doesn't cause any damage to a neighboring tissue and forms direct bonding with a natural bone. However, the mechanical properties (e.g. strength, fracture toughness) of the HAp are poor as described above. Poor mechanical properties of HAp cast limitations to wider application. Therefore, the embodiment of the present invention reinforces the HAp by addition of secondary phase as reinforcement.

The secondary phase as reinforcement should have some properties as follows.

Firstly, the strength and the elastic modulus of the secondary phase should be higher than those of the matrix phase.

Secondly, the interfacial strength between the matrix phase and the secondary phase should be neither too weak nor too strong. For an appropriate interfacial strength, no excessive reaction should occur between the matrix phase and the secondary phase.

Thirdly, the coefficient of thermal expansion of the secondary phase should not differ too much from that of the matrix phase. Otherwise, subsequent to densification, microcracks will form around the second phase during cooling and seriously deteriorate the mechanical properties of the composite material.

Fourthly, the secondary phase should have biocompatibility.

As a material that has all the above-described properties, there are some kinds of ceramic material such as silicon carbide SiC, silicon nitride $Si_3N_4$, zirconia $ZrO_2$ and metal fiber. In particular, tetragonal zirconia($ZrO_2$) polycrystal (hereinafter, referred to as 'TZP') is used secondary phase according to the embodiment of the present invention. The TZP has partially stabilized phase.

Partially stabilized zirconia has been commonly used as reinforcement for many ceramics because of its high strength and fracture toughness. Bioinertness is another merit of the $ZrO_2$. However, extensive interfacial reaction between the HAp and the $ZrO_2$ to form tricalcium phosphate $Ca_3(PO_4)_2$ (hereinafter, referred to as 'TCP') and fully stabilized $ZrO_2$ during mixing and sintering is a serious problem because the tricalcium phosphate leads to a serious reduction in the bioactivity and biocompatibility of the HAp. In addition, the extensive interfacial reaction between the HAp and the. $ZrO_2$ leads to deterioration of mechanical properties of the composite.

For example, the strength of the composite increased to about 150 MPa when 10 vol % $ZrO_2$ is added to HAp. However, further addition of $ZrO_2$ particles reduces the strength to the level of pure HAp. And the strength of HAp decreases with increasing the sintering temperature in spite of the general fact that the denser a specimen the higher a sintering temperature.

The above-mentioned deterioration of mechanical properties of the composite results from the facts that follow.

Higher temperature causes the HAp matrix phase to decompose into β-TCP, which plays a role of fracture origin in a composite. This vigorous decomposition with $ZrO_2$ would reduce the strength of HAp; CaO, as the decomposition by-product, diffused into the $ZrO_2$ secondary phase and stabilized the TZP into cubic phase.

So as to avoid the above-mentioned side reaction, barrier layer is introduced in the present invention. When the direct contact of $ZrO_2$ with HAp is avoided by coating the $ZrO_2$ powder with barrier layer, the deleterious interfacial reaction between the HAp and $ZrO_2$ can be prevented. In this case, the toughening/strengthening effect of TZP is preserved.

Material such as silica $SiO_2$, magnesia MgO and alumina $Al_2O_3$ can be used as the barrier layer. In particular, alumina is used as the barrier layer according to the embodiment of the present invention. Alumina is classified as a bioinert material. Since alumina has less tendency of decomposing the HAp matrix phase into β- TCP, it can prevent fracture of a composite and improve the mechanical properties of the composite.

In the present embodiment, the zirconia is added into a composite by 3 vol % to 50 vol %, preferably 10 vol % to 20 vol %, and the alumina is added into the composite by 3 vol % to 50 vol %, preferably 20 vol % to 50 vol %.

A fabrication method of a sintered ceramic composite implant material in accordance with the preferred embodiment of the present invention will now be described with reference to FIG. 1.

As a first step, zirconia powder is prepared as reinforcement which forms secondary phase of a composite.

As a second step, alumina precursor powder is prepared. The alumina precursor powder is for forming barrier layer of the composite. The alumina precursor is a material which converts into alumina during a sintering and can be replaced with alumina. There are several methods such as sol-gel method, precipitation method and hydrolysis method with which alumina precursor is generated. Particularly, in the present embodiment, the hydrolysis method is used to generate alumina precursor.

The examples of the methods to obtain the alumina precursor are as follows: heat treatment of aluminum acetate oxide $Al_2O(OOCCH_3)_4$ with distilled water in an autoclave, hydrolysis of a variety of aluminum compounds such as aluminum t-butoxide $Al[OC(CH_3)_3]_3$, aluminum sec-butoxide $Al[O(CH_3)CHC_2H_5]_3$, aluminum n-butoxide $Al[O(CH_2)_3]_3$, aluminum ethoxide $Al(OC_2H_5)_3$, aluminum hydroxide $Al(OH)_3$, aluminum lactate $Al[CH_3CH(OH)CO_2]_3$, aluminum sulfate $Al_2(SO_4)_3$, aluminum tartrate $Al_2(C_4H_4O_6)_3$, aluminum isopropoxide $Al[OCH(CH_3)_2]_3$, and precipitation of aluminum compounds such as aluminum nitrate $Al(NO_3)_3$ dissolved in a base-added water. Particularly, in the present embodiment, boehmite generated by hydrolyzing an aluminum isopropoxide $Al(OCH(CH_3)_2)_3$ is used as an alumina precursor. Heat treatment is carried out at 60° C.~100° C. during the above-mentioned hydrolysis of aluminum isopropoxide. Boehmite, alumina precursor, which is obtained by this process transforms to alumina during a sintering.

As a third step, a suspension is prepared by dispersing the zirconia powder and the alumina precursor in an aqueous solution by which the zirconia powder is coated with the alumina precursor. Oxide ceramics acquire a surface charge when they are dispersed in an aqueous solution and become a colloidal suspension. It is because the oxide surfaces are hydrated-combined with $OH^{31}$ ions, and this group leads to a positively or negatively charged surface depending on the pH of the solution by adsorption of $H^+$ions or dissociation of $H^+$ions (adsorption of $OH^-$ions). Accordingly, the surface of zirconia powder and the surface of alumina precursor are charged with different sign from each other by controlling the pH of the suspension. The pH of the suspension is controlled by lowering the pH by adding an acid such as HCl, $H_2SO_4$, $HNO_3$ or by raising the pH by adding a base such as $NH_4OH$, NaOH.

Figure 2:
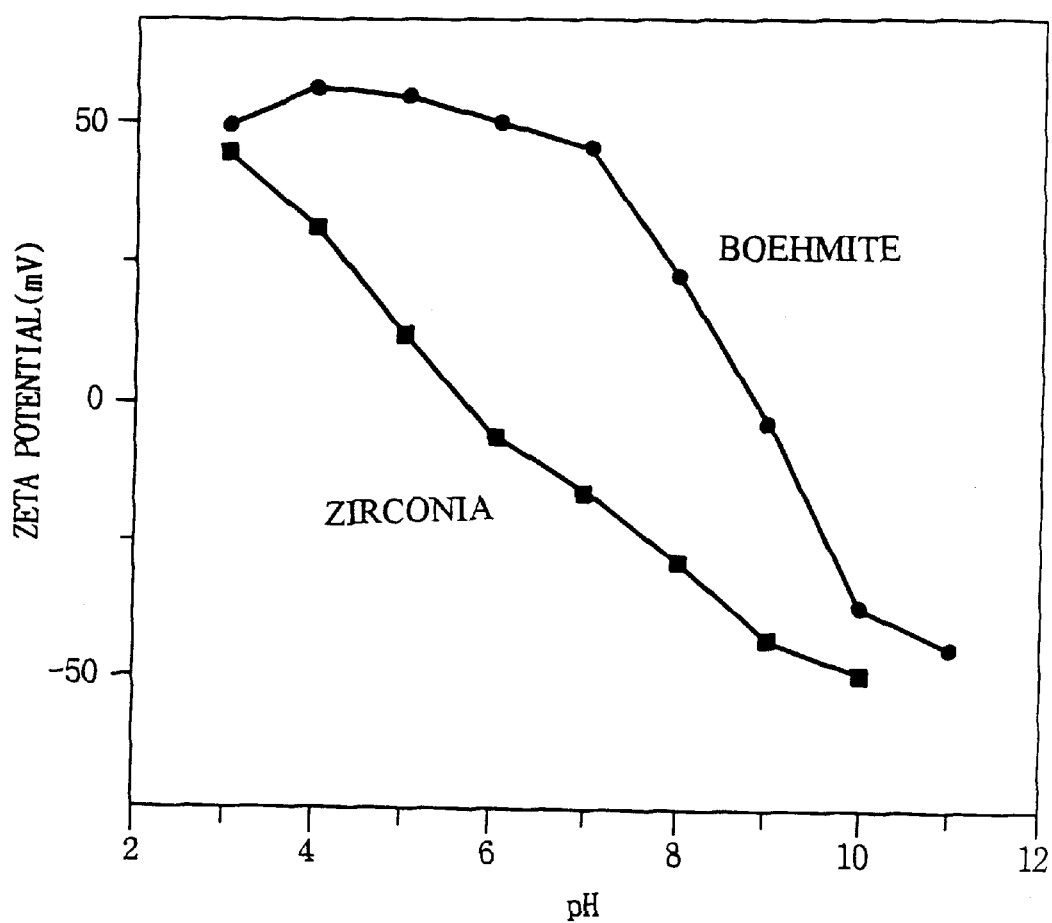
FIG. 2 is a graph illustrating Zeta potential changes of zirconia powder and alumina precursor responding to the change of pH of an aqueous solution.

FIG. 2 illustrates Zeta potential changes of the zirconia powder and the boehmite responding to the change of pH of an aqueous solution. The points of zero charge of the zirconia and the boehmite are about 5 and about 9, respectively. Therefore, if the pH of the suspension is maintained between about 5 and about 9, alumina precursor is charged with (+) and zirconia is charged with (−). Thus, there are two kinds of interaction to occur: the electrostatic attraction between (+) and (−) charged particles, which causes to occur heterocoagulation between the zirconia and the boehmite and makes the zirconia coated with boehmite, and the electrostatic repulsion between same-charged particles, which promotes good dispersion. In this embodiment, a boehmite suspension is added dropwise to a zirconia suspension while stirring vigorously and maintaining the pH of the suspension at 7.5. After adding the suspension, the mixture is stirred for extended periods of time for complete coagulation.

As a fourth step, the coated powder obtained by the above-mentioned method, is filtered, dried at 50° C.~100° C. for 1~10 hours and calcined at 400° C.~600° C. for 1 hour~10 hours.

Figure 3:
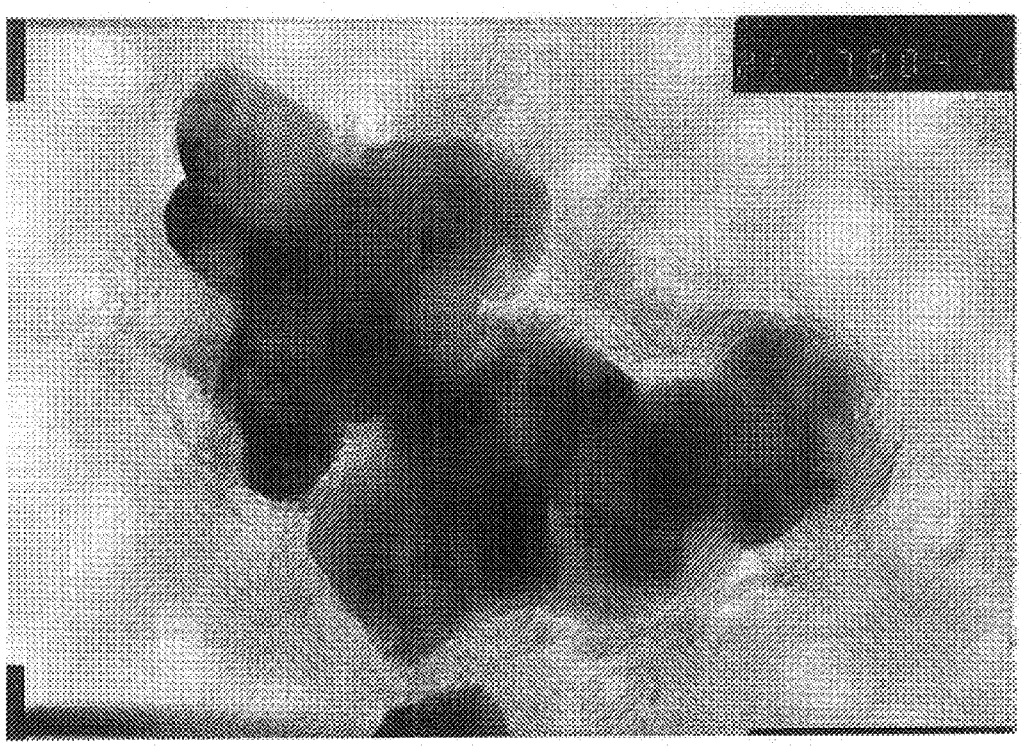
FIG. 3 is a TEM micrograph illustrating zirconia powder coated with alumina precursor after calcination according to an embodiment of the present invention.

FIG. 3 illustrates TEM micrograph of zirconia powder coated with boehmite after calcination.

As illustrated in FIG. 3, the boehmite calcined has a shape of fiber network, and these fibrils interpenetrate the gaps of zirconia agglomerates and coat zirconia powders well. The micrograph shows that the boehmite adheres uniformly to the zirconia.

As a fifth step, the coated powder obtained in the fourth step is premixed with HAp powder and then, the premixed powder is mixed by ball milling in distilled water for about 24 hours, and then the above-mentioned mixture slurry is dried and sieved.

Finally, as a sixth step, the mixture slurry obtained in the fifth step is hot pressed at 1000° C.~1400° C. for 30 minutes~3 hours in flowing inert gas atmosphere such as Ar with an applied pressure of 10 MPa~30 MPa. Although the hot pressing is used in the present embodiment, a variety of pressing and sintering method such as hot isostatic pressing, pressureless sintering or the like can also be used instead.

The characteristics of a sintered ceramic composite implant material according to the embodiment of the present invention will now be described with reference to FIG. 4~FIG. 7.

Figure 4:
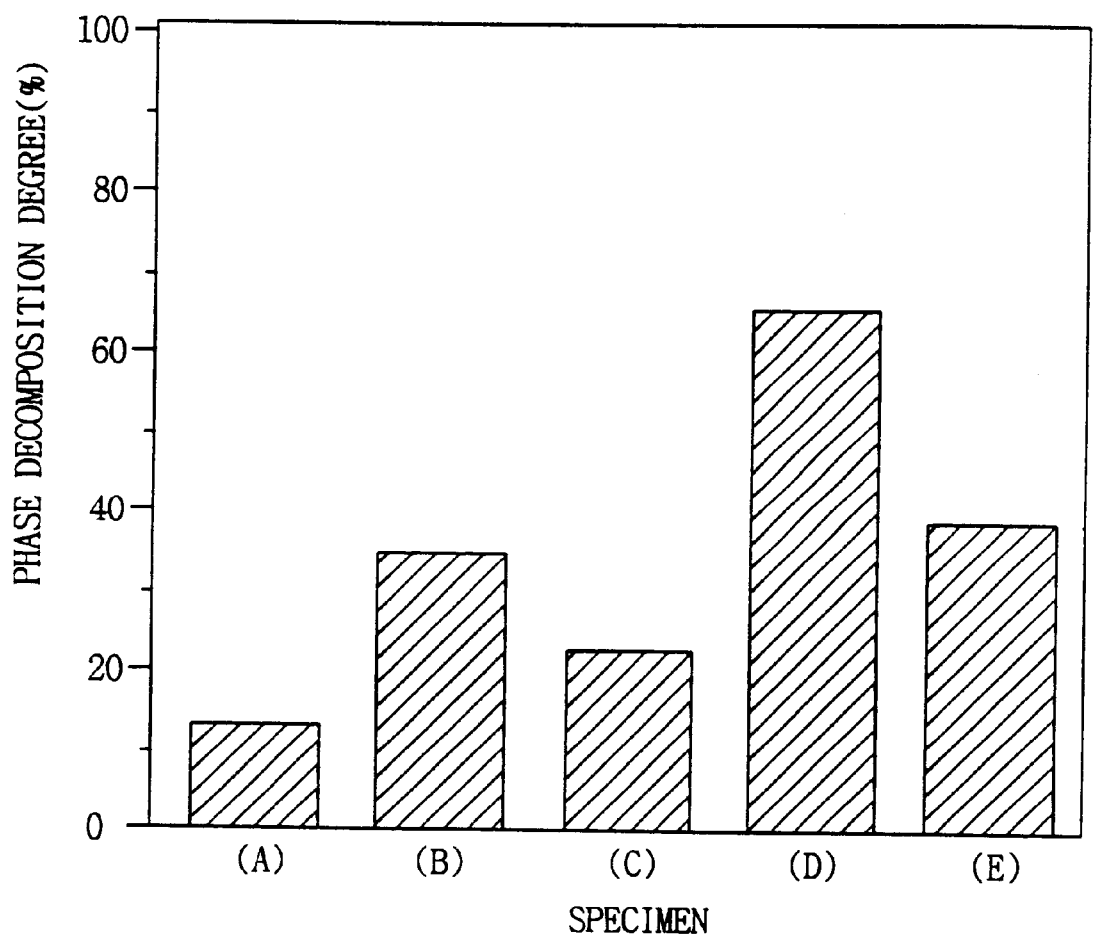
FIG. 4 is a graph illustrating phase decomposition degree of a sintered ceramic composite implant material according to an embodiment of the present invention.

FIG. 4 illustrates relative amount of TCP to HAp deduced from XRD patterns. In order to estimate the degree of interfacial reaction between the HAp matrix phase and the secondary phase and the degree of decomposition of HAp, the relative amount of TCP to HAp was deduced from the intensities of HAp peaks and TCP peaks by X-ray diffraction analyses.

In FIG. 4, specimen A is hot-pressed pure HAp, specimen B is hot-pressed HAp with 10 vol % zirconia, specimen C is hot-pressed HAp with 20 vol % alumina and specimen D is hot-pressed HAp with 10 vol % zirconia and 20 vol % alumina by conventional mixing. In the specimen D, the zirconia secondary phase is not coated with alumina. Specimen E, a specimen according to the present embodiment, is hot-pressed HAp with 10 vol % zirconia and 20 vol % alumina, in which the zirconia secondary phase is coated with alumina barrier layer. The difference between specimen D and specimen E is whether the alumina powder coats the zirconia powder or not.

As illustrated in FIG. 4, the decomposition degree of the HAp happened in the specimen B is higher than that of specimen A by twice or more. This is because there happens an interfacial reaction between the HAp matrix phase and the zirconia secondary phase as described above. The degree of decomposition degree of HAp happened in the specimen C is also higher than that of specimen A, but is lower than that of specimen B. In the case of specimen D with an addition of 10 vol % zirconia and 20 vol % alumina by conventional mixing, the degree of decomposition is higher than the sum of those of specimen B and specimen C. However, the decomposition degree of specimen E according to the present embodiment is much lower than that of specimen D because the 20 vol % alumina barrier layer restrain the interfacial reaction between the HAp matrix phase and the zirconia secondary phase. In other words, the alumina barrier layer effectively prevents the decomposition of HAp matrix phase.

Figure 5:
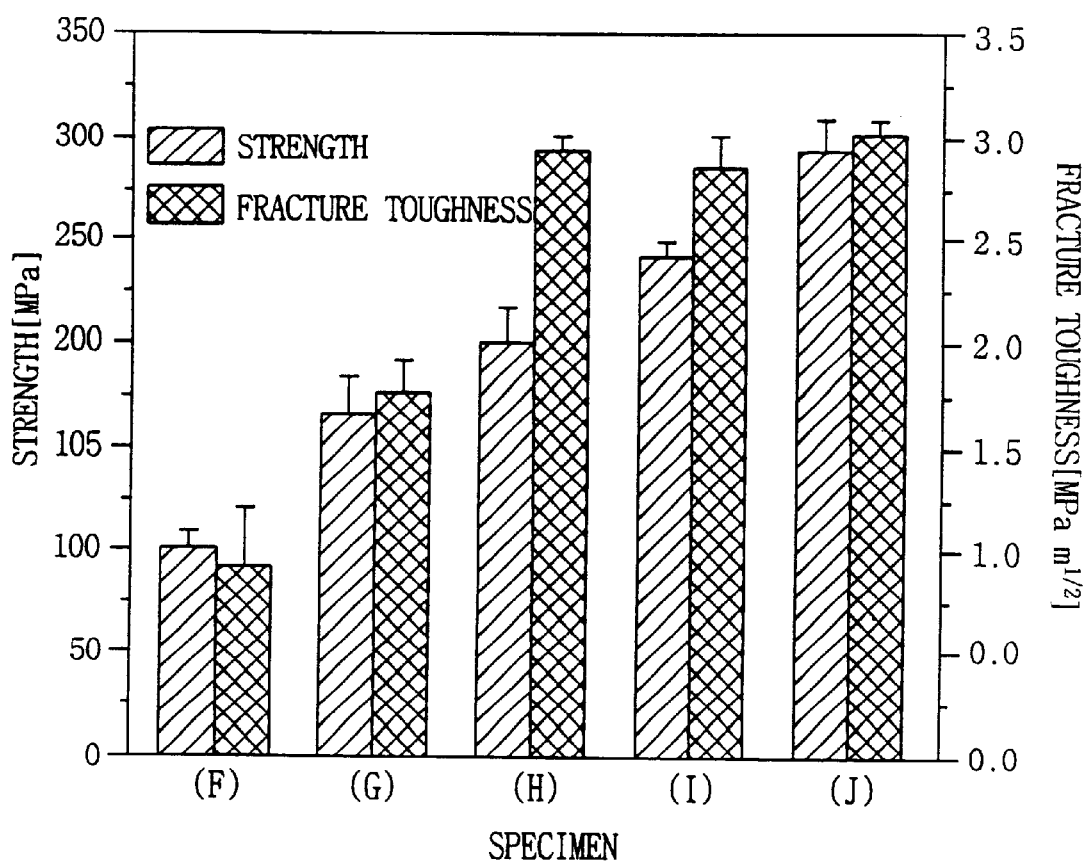
FIG. 5 is a graph illustrating mechanical properties of a sintered ceramic composite implant material according to an embodiment of the present invention.

FIG. 5 illustrates the mechanical properties of a specimen composed of pure HAp and four specimens containing various content of zirconia secondary phase and alumina barrier layer according to the present embodiment.

In the FIG. 5, the specimen F is hot-pressed pure HAp, the specimen G is hot-pressed HAp with an addition of 3 vol % zirconia secondary phase and 3 vol % alumina barrier layer, the specimen H is hot-pressed HAp with an addition of 10 vol % zirconia secondary phase and 20 vol % alumina barrier layer, the specimen I is hot-pressed HAp with an addition of 15 vol % zirconia secondary phase and 15 vol % alumina barrier layer, the specimen J is hot-pressed HAp with an addition of 15 vol % zirconia secondary phase and 30 vol % alumina barrier layer. The mechanical strength and fracture toughness of the above-described specimens are represented with a bar chart respectively.

As illustrated in FIG. 5, all the specimens with an addition of zirconia secondary phase and alumina barrier layer show better mechanical strength and fracture toughness than specimen F of pure HAp. Accordingly, it is apparent that the present invention improves the mechanical properties of a sintered ceramic composite implant material. From the fact that as much zirconia added as higher mechanical strength of composite, zirconia plays an important role in improving mechanical strength of composite. And, from the fact that as much alumina added as higher fracture toughness of composite, alumina plays an important role in improving fracture toughness of a composite by restraining interfacial reactions between HAp matrix phase and zirconia secondary phase.

Among the above-described specimens, specimen J shows flexural strength of about 300 MPa and fracture toughness of 3 MPa·m$^{1/2}$. This result means that the mechanical properties of the HAp can be increased by a factor 3 by the addition of zirconia powder coated with alumina and be higher than the minimum fracture toughness 2 MPa·m$^{1/2}$ which is needed for hard tissue implant.

Figure 6:
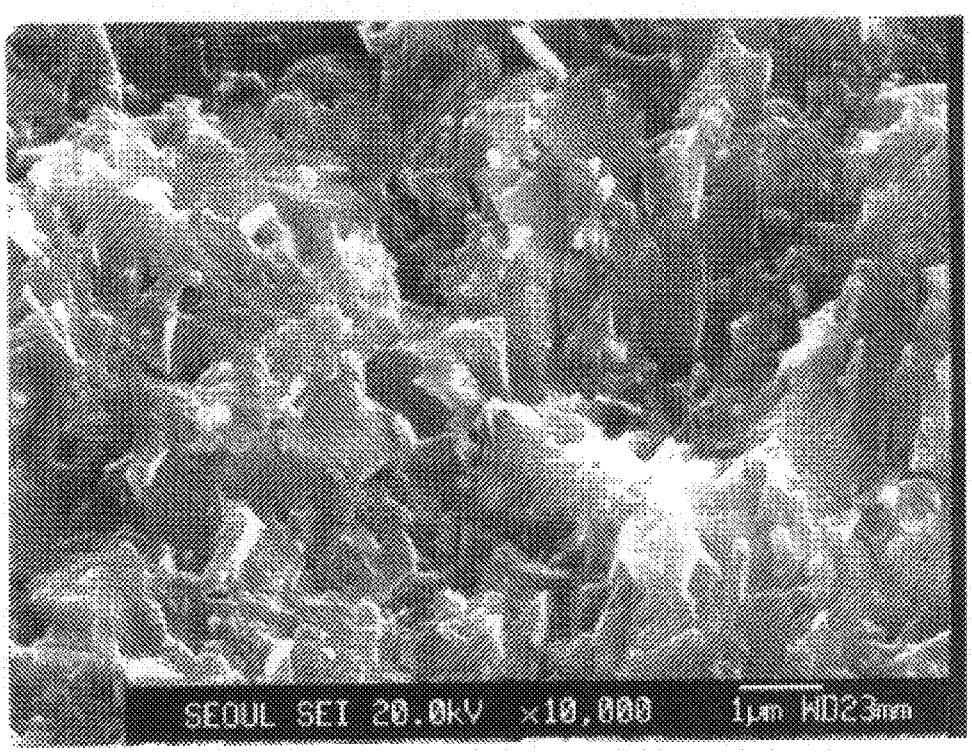
FIG. 6 is a SEM micrograph illustrating a fracture surface of a sintered ceramic composite implant material according to an embodiment of the present invention.

FIG. 6 illustrates a SEM micrograph of fracture surface of a composite according to the present embodiment.

When 10 vol % zirconia and 20 vol % alumina are added in accordance with the present embodiment, the fracture pattern is changed remarkably. That the fracture mode changes from transgranular to intergranular interprets the enhancement of $K_{IC}$, as illustrated in FIG. 6. In the case in which coated zirconia powder is added as a reinforcement, the HAp composite have enough interfacial strength for the crack to propagate through the grain boundary—intergranular fracture. And there happened less micropores in the sintered specimen than in the composite fabricated by the conventional mixing method, which means that there is less deleterious reaction in the HAp composite.

Figure 7:
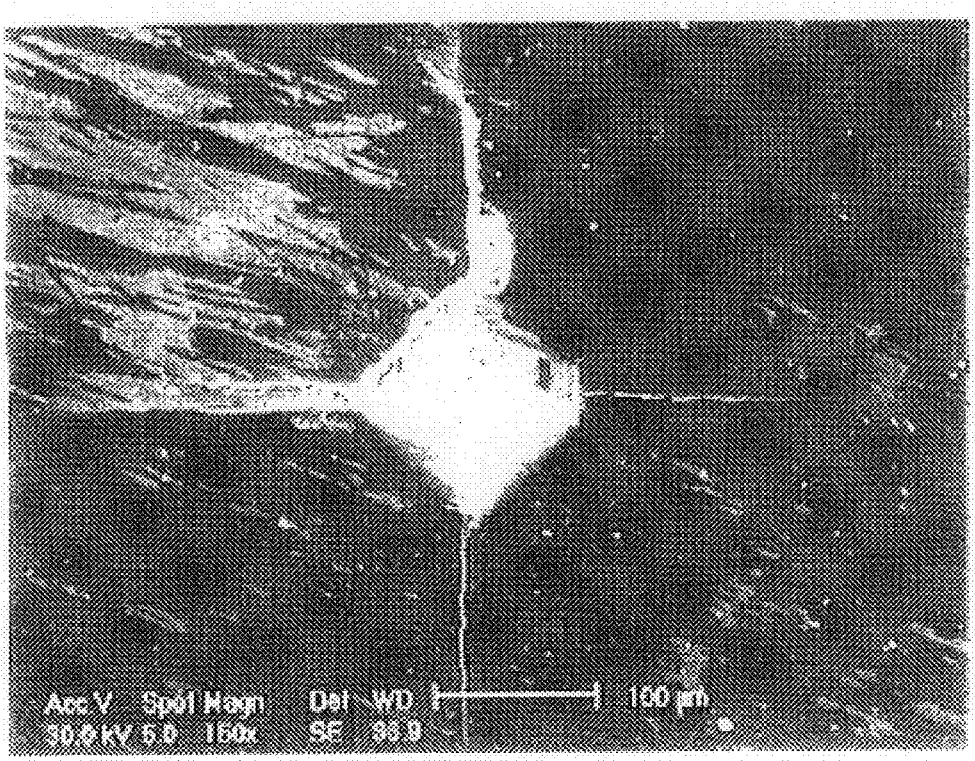
FIG. 7 is a SEM micrograph illustrating a surface of a sintered ceramic composite implant material according to an embodiment of the present invention after Vickers' indentation with load of 98 N.

FIG. 7 illustrates a SEM micrograph after Vickers indentation with load of 98 N. When the specimen containing 10 vol % zirconia and 20 vol % alumina in accordance of the present embodiment is indented with the load of 10 kg, chipping is not observed around the indent. The observed improvement in the fracture toughness by the reinforcement is again well illustrated by this micrograph.

A sintered ceramic composite implant material according to the present invention has several advantages. First, since ceramic reinforcement is used in a composite, and thus it is possible to compensate for poor mechanical properties of apatite while utilizing bioactivity and biocompatibility of apatite.

In addition, by restraining interfacial reactions between ceramic reinforcement and apatite, it is possible to solve the problem caused by the above-described interfacial reaction.

Further, since the reinforcement according to the present invention is composed of ceramic having similar mechanical and thermal properties to those of apatite, it is possible to solve a problem caused by differences in physical and thermal properties.

Furthermore, since the present invention uses reinforcement having bioinertness, it is possible not to deteriorate biocompatibility of apatite.

It will be apparent to those skilled in the art that various modifications and variations can be made to a sintered ceramic composite implant material, and the preparation method thereof, embodying the present invention without departing from the spirit or scope of the invention. Thus, it is intended that the present invention covers the modifications and variations of this invention provided they come within the scope of the appended claims and their equivalents.

The foregoing embodiments are merely exemplary and/or illustrative, and the description given herein is not intended to limit the scope of the claims. Many alternatives, modifications, and variations will be apparent to those skilled in the art.

What is claimed is:

1. A method for fabricating a sintered ceramic composite implant material, comprising the steps of:

providing reinforcement powder coated with barrier layer;

forming a mixture by mixing the coated reinforcement powder with apatite powder; and sintering the mixture.

2. A method for fabricating a sintered ceramic composite implant material according to claim 1, wherein the reinforcement powder comprises at least one of SiC, silicon nitride $Si_3N_4$, zirconia $ZrO_2$ and metal fiber.

3. A method for fabricating a sintered ceramic composite implant material according to claim 1, wherein the barrier layer comprises at least one of alumina $Al_2O_3$, silica $SiO_2$ and magnesia MgO.

4. A method for fabricating a sintered ceramic composite implant material according to claim 1, wherein the reinforcement powder providing comprises the sub-steps of:

providing reinforcement powder;

providing barrier layer powder;

coating the reinforcement powder with the barrier layer powder in a suspension including the reinforcement powder and the barrier layer powder; and drying and calcining the reinforcement powder coated with the barrier layer powder.

5. A method for fabricating a sintered ceramic composite implant material according to claim 4, wherein the calcination is carried out at 400° C.~600° C.

6. A method for fabricating a sintered ceramic composite implant material according to claim 4, wherein the reinforcement powder and the barrier layer powder are charged with different sign from each other by controlling the pH of the suspension.

7. A method for fabricating a sintered ceramic composite implant material according to claim 6, the pH of the suspension is controlled to be 5~9.

8. A method for fabricating a sintered ceramic composite implant material according to claim 4, wherein the barrier layer powder comprises precursor that converts into the material of which the barrier layer is composed.

9. A method for fabricating a sintered ceramic composite implant material according to claim 8, wherein the precursor is alumina precursor.

10. A method for fabricating a sintered ceramic composite implant material according to claim 9, wherein the alumina precursor is fabricated by a method selected from the group consisting of sol-gel method, precipitation method and hydrolysis method.

11. A method for fabricating a sintered ceramic composite implant material according to claim 1, wherein the mixture forming step comprises the sub-steps of:

premixing the reinforcement powder with the barrier layer powder;

forming a mixture by mixing the premixed powder by ball milling; and drying and sieving the mixture.

12. A method for fabricating a sintered ceramic composite implant material according to claim 1, wherein the sintering step is carried out by hot pressing the mixture in an inert gas atmosphere.

13. A method for fabricating a sintered ceramic composite implant material according to claim 12, wherein the hot pressing is carried out at 1000° C.~1400° C. with an applied pressure of 10 MPa~30 MPa.

* * * * *